United States Patent [19]

Chenard

[11] Patent Number: 5,306,723
[45] Date of Patent: Apr. 26, 1994

[54] NEUROPROTECTIVE INDOLONE AND RELATED DERIVATIVES

[75] Inventor: Bertrand L. Chenard, Waterford, Conn.

[73] Assignee: Pfizer Inc., New York, N.Y.

[21] Appl. No.: 941,118

[22] PCT Filed: Mar. 4, 1991

[86] PCT No.: PCT/US91/01470
§ 371 Date: Nov. 6, 1992
§ 102(e) Date: Nov. 6, 1992

[87] PCT Pub. No.: WO91/17156
PCT Pub. Date: Nov. 14, 1991

[51] Int. Cl.$^5$ .................. A61K 31/44; C07D 209/34; C07D 401/06; C07D 263/58
[52] U.S. Cl. ................... 514/304; 514/323; 514/324; 514/312; 546/126; 546/198; 546/201; 546/153
[58] Field of Search ............ 546/126, 153, 198, 201; 514/304, 323, 324, 312

[56] References Cited

U.S. PATENT DOCUMENTS

| | | | |
|---|---|---|---|
| 3,294,804 | 12/1966 | Carabateas | 260/294.3 |
| 3,509,164 | 4/1970 | Carron et al. | 260/294.7 |
| 4,082,755 | 4/1978 | van Wijngaarden | 546/199 |
| 4,304,915 | 12/1981 | Berthold | 546/201 |
| 4,358,456 | 11/1982 | Ward | 514/323 |
| 4,393,069 | 7/1983 | Langbein et al. | 424/265 |
| 5,034,401 | 7/1991 | Frost et al. | 514/323 |

FOREIGN PATENT DOCUMENTS

| | | | |
|---|---|---|---|
| 202164 | 11/1986 | European Pat. Off. | C07D 211/32 |
| 322361 | 12/1987 | European Pat. Off. | C07D 405/04 |
| 2546166 | 11/1984 | France | C07D 211/14 |

OTHER PUBLICATIONS

CA116(9):83552u Preparation ... as Neuroprotectants, Chenard, p. 807, 1992.
Gotti et al., J. Pharmacol. Exp. Therap., vol. 247, pp. 1211–1222 (1988).
Carter et al., J. Pharmacol. Exp. Therap., vol. 247, pp. 1222–1232 (1988).
CA86:189738m Carbostyril Derivatives. Nakagawa et al., p. 592, 1977.
CA89:43498y; Derwent 14858A Piperazinyl ... acetophenone. Muro et al., p. 644, 1978.
CA89:146938w; Derwent 48671A Aminoalcohol derivatives. Muro et al., p. 615, 1978.
Carron et al., Arneim-Forsch., vol. 21, pp. 1992–1998 (1971), Synthesis ... Derivatives.
Bonte et al., Eur. J. Med. Chem., 25(4), pp. 361–368 (1990) Amino Ketone ... properties.

Primary Examiner—Mary C. Lee
Assistant Examiner—Joseph K. McKane
Attorney, Agent, or Firm—Peter C. Richardson; J. Trevor Lumb; Gregg C. Benson

[57] ABSTRACT

5-(1-Hydroxy-2-piperidinopropyl)-2(1H,3H)-indolone derivatives and analogs; pharmaceutical compositions thereof; methods of treating CNS disorders therewith; and intermediates useful in the preparation of said compounds.

55 Claims, No Drawings

NEUROPROTECTIVE INDOLONE AND RELATED DERIVATIVES

BACKGROUND OF THE INVENTION

The present invention is directed to neuroprotective (antiischemic and excitatory aminoacid receptor blocking) 5-(1-hydroxy-2-piperidinopropyl)-2(1H,3H) -indolone analogs, defined by the formula (I), (II) and (III) below; pharmaceutically acceptable salts thereof; a method of using these compounds in the treatment of stroke, traumatic brain injury or CNS degenerative diseases such as Alzheimer's disease, senile dementia of the Alzheimer's type, Huntington's disease and Parkinson's disease; and to certain intermediates therefor.

Ifenprodil is a racemic, so-called dl-erythro compound having the relative stereochemical formula

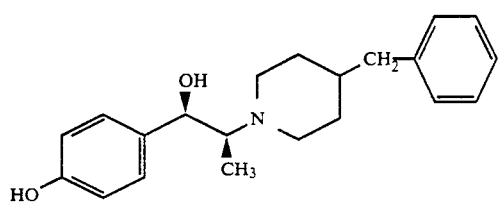

which is marketed as a hypotensive agent, a utility shared by a number of close analogs; Carron et al., U.S. Pat. No. 3,509,164; Carron et al., Drug Res., v. 21, pp. 1992-1999 (1971). Ifenprodil has also been shown to possess antiischemic and excitatory aminoacid receptor blocking activity; Gotti et al., J. Pharm. Exp. Therap., v. 247, pp. 1211-21 (1988); Carter et al., loc. cit., pp. 1222-32 (1988). See also published European patent application 322,361 and French Patent 2546166. A goal, substantially met by the present invention, has been to find compounds possessing such neuroprotective effect in good measure, while at the same time having lowered or no significant hypotensive effect.

Certain structurally related 1-phenyl-3-(4-aryl -4-acyloxypiperidino)-1-propanols have also been reported to be useful as analgesics, U.S. Pat. No. 3,294,804; and 1-[4-(amino- and hydroxy-alkyl)phenyl]-2-(4-hydroxy -4-tolylpiperazino)-1-alkanols and alkanones have been reported to possess analgesic, antihypertensive, psychotropic or antiinflammatory activity, Japanese Kokai 53-02,474 (CA 89:43498y; Derwent Abs. 14858A), 53-59,675 (CA 89:146938w; Derwent Abs. 48671A) and 76,118,772 (CA 86:189738m).

More recently, in published European Patent Application No. 351,282, compounds which include those of the formula

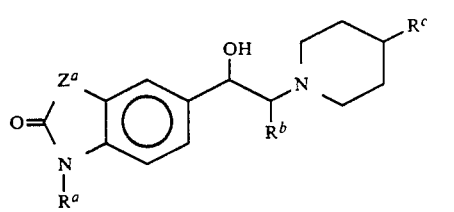

wherein $R^a$ and $R^b$ are each independently hydrogen or $(C_1-C_4)$alkyl, $R^c$ is benzyl, phenoxy, benzyloxy or phenoxymethyl, and $Z^a$ is $CH_2$, $C(CH_3)_2$ or $CH_2CH_2$, have been reported as having neuroprotective type activity.

Also, amino ketone and amino alcohol derivatives of benzoxazolinone and their adrenergic and antihypertensive properties are described in the European Journal of Medicinal Chemistry, 25, 361-368, (1990), C.A. 113:191213f.

The nomenclature used herein is generally that of Rigaudy et al., IUPAC Nomenclature of Organic Chemistry, 1979 Edition, Pergammon Press, New York. 2(1H,3H)-Indolones are alternatively named as oxindoles.

SUMMARY OF THE INVENTION

The present invention is directed to racemic or optically active compounds of the formulas

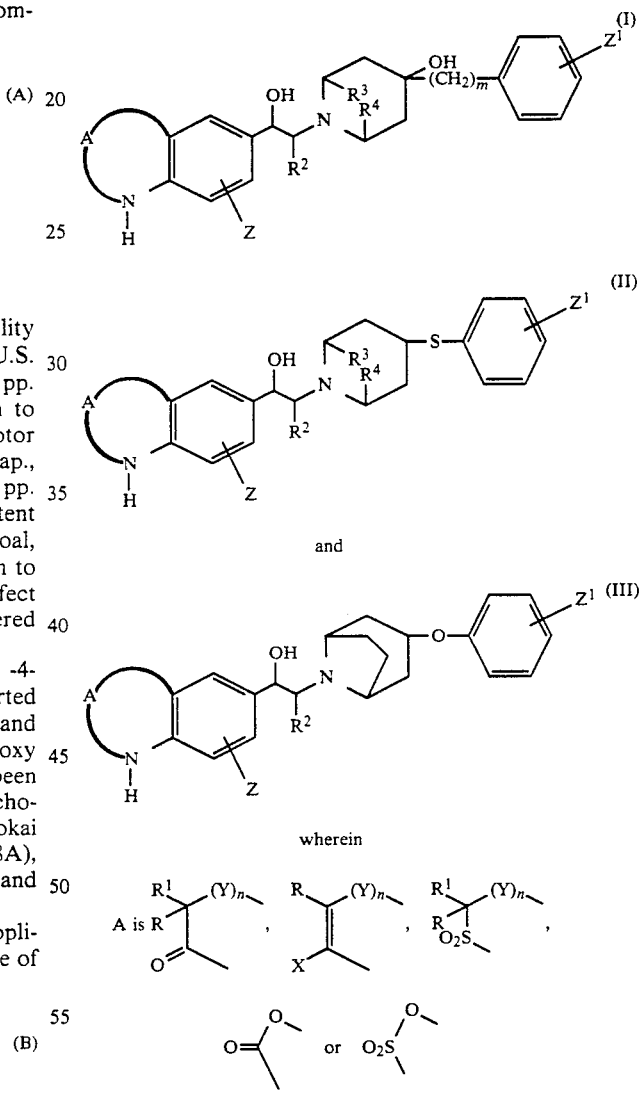

wherein

A is 
$$R^1\underset{O}{\overset{}{\underset{\|}{C}}}\underset{}{\overset{(Y)_n}{\diagdown}} , \quad R\underset{X}{\overset{}{\underset{\|}{C}}}\underset{}{\overset{(Y)_n}{\diagdown}} , \quad \underset{R}{\overset{R^1}{\underset{O_2S}{\diagdown}}}\underset{}{\overset{(Y)_n}{\diagdown}} ,$$

$$O=\overset{O}{\underset{}{\diagup}}\underset{}{\diagdown} \quad \text{or} \quad O_2S\overset{O}{\underset{}{\diagup}}\underset{}{\diagdown}$$

n is 0 or 1;
m is 0 or an integer from 1-6;
R, $R^1$ and $R^2$ are each independently hydrogen or $(C_1-C_3)$alkyl;
$R^3$ and $R^4$ are taken separately and are each hydrogen, or $R^3$ and $R^4$ are taken together and are ethylene;
X is hydrogen, $(C_1-C_3)$alkoxy]-carbonyl;
Y is $CH_2$ or oxygen;

Z and $Z^1$ are each independently hydrogen, ($C_1$-$C_3$)alkyl, ($C_1$-$C_3$)alkoxy, fluoro, chloro or bromo;

and the pharmaceutically-acceptable acid addition salts thereof.

The preferred compounds of the present invention generally have $R^2$ as hydrogen or methyl, most preferably as methyl, having relative stereochemistry in 1-hydroxypropyl side chain depicted as

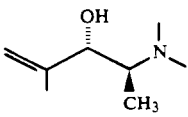

and which is specified either as (1S*,2S*) or (1R*,2R*).

The preferred values of A are generally

 (forming a 2(1H,3H)-indolone or oxindole);

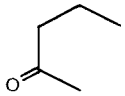 (forming a 3,4-dihydro-2(1H)-quinolone);

 (forming an indole);

and

 (forming a 2(3H)-benzoxazolone).

The present invention is also directed to intermediate compounds of the formula

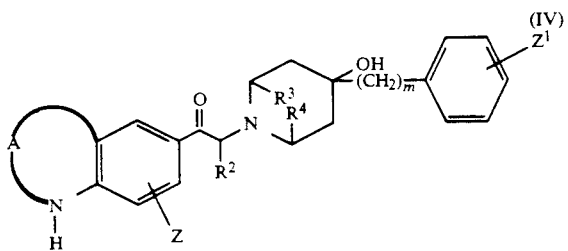 (IV)

and

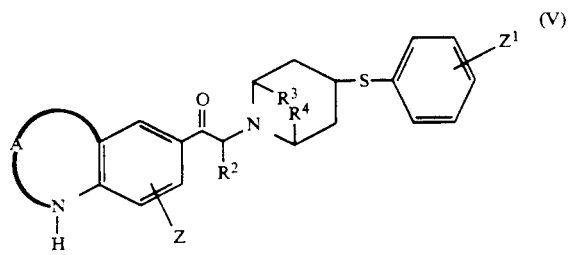 (V)

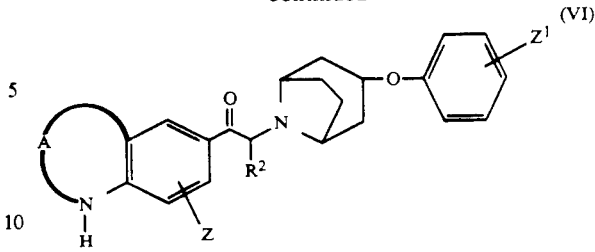 (VI)

wherein the variable groups are as defined above.

The present invention is further directed to pharmaceutical compositions comprising a compound of the formula (I), (II) or (III), and to a method of treating stroke, traumatic brain injury or a CNS degenerative disease with a compound of the formula (I), (II) or (III).

The expression "pharmaceutically-acceptable acid addition salts" is intended to include but is not limited to such salts as the hydrochloride, hydrobromide, hydroiodide, nitrate, hydrogen sulfate, dihydrogen phosphate, mesylate, maleate and succinate. Such salts are conventionally prepared by reacting the free base form of the compound (I), (II) or (III) with an appropriate acid, usually one molar equivalent, and in a solvent. Those salts which do not precipitate directly are generally isolated by concentration of the solvent and/or addition of a non-solvent.

It will be noted that those compounds of the formula (I) to (VI) which, in the central portion of the molecule, are 1-alkanols possess an asymmetric C-1 carbon, while those wherein R is other than hydrogen possess a second asymmetric center at the C-2 carbon of the alkanol. Similarly, in those compounds of the formulas (IV) to (VI) which are 1-alkanones wherein R is other than hydrogen possess a C-2 asymmetric carbon. It will be evident to those skilled in the art of organic chemistry, therefore, that such compounds can be resolved into optical isomers showing equal but opposite rotation of plane polarized light. For example, all of these compounds are potentially resolved by fractional crystallization of their diastereomeric addition salts with an optically active acid, as exemplified below. The alcohols are also potentially resolved by chromatography or fractional crystallization of esters or urethanes derived by reaction with activated forms of optically active acids or with optically active isocyanates, as also exemplified below. Thus, the present invention should not be construed as limited to the racemic forms of the present compounds.

DETAILED DESCRIPTION OF THE INVENTION

The compounds of the present invention, having the formula (I), (II) and (III) defined above, are readily prepared.

The precursor ketones are generally prepared by nucleophilic displacement of an appropriately substituted 2-halo, 2-alkanesulfonyloxy- or 2-arylsulfonyloxy-1-alkanone with an appropriately substituted piperidine derivative, e.g.,

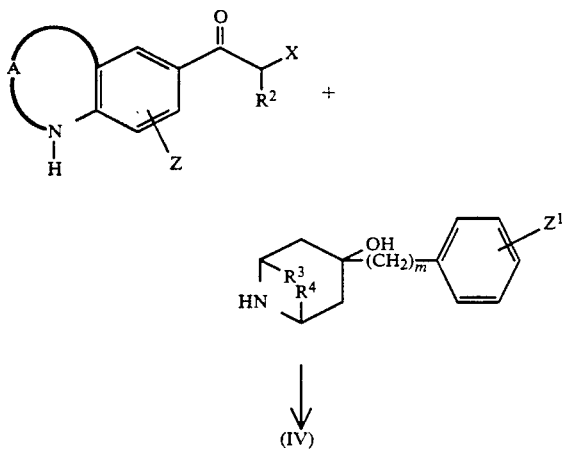

wherein X is typically chloro, bromo, mesyloxy or tosyloxy. This reaction is carried out under conditions typical of nucleophilic displacements in general. Where the two reactants are about equivalent in availability, close to substantially molar equivalents may be used; although when one is more readily available, it is usually preferred to use that one in excess, in order to force this bimolecular reaction to completion in a shorter period of time. The reaction is generally carried out in the presence of at least 1 molar equivalent of a base, the piperidine derivative itself, if it is readily available, but more usually a tertiary amine which is at least comparable in base strength to the nucleophilic piperidine; and in a reaction inert solvent such as ethanol. If desired, the reaction is catalyzed by the addition by the addition of up to one molar equivalent or more of an iodide salt (e.g., NaI, KI). Temperature is not critical, but will generally be somewhat elevated in order to force the reaction to completion within a shorter time period, but not so high as to lead to undue decomposition. A temperature in the range of 50°–120° C. is generally satisfactory. Conveniently, the temperature is the reflux temperature of the reaction mixture.

As used in the preceding paragraph, and elsewhere herein, the expression "reaction inert solvent" refers to any solvent which does not interact with starting materials, reagents, intermediates or products in a manner which adversely affects the yield of the desired product.

The resulting ketone intermediates are conveniently converted to corresponding alcohols by conventional reduction with $NaBH_4$, usually in excess, in a protic solvent such as methanol or ethanol, generally at temperature in the range of about 15°–45° C.

The starting materials and reagents required for the synthesis of the compounds of the present invention are readily available, either commercially, according to literature methods, or by methods exemplified in Preparations below.

The present compounds of the formula (I), (II) and (III) possess selective neuroprotective activity, based upon their antiischemic activity and ability to block excitatory aminoacid receptors, while at the same time generally having lowered or no significant hypotensive activity. The antiischemic activity of the present compounds is determined according to one or more of the methods which have been detailed previously by Gotti et al. and Carter et al. cited above, or by similar methods. The ability of the compounds of the Present invention to block excitatory amino acid receptors is demonstrated by their ability to block N-methyl-D-aspartic acid-induced (NMDA) elevations of cGMP in neonatal rat cerebellums according to the following procedure. Cerebellums from ten 8-14 day old Wistar rats are quickly excised and placed in 4° C. Krebs/bicarbonate buffer, pH 7.4 and then chopped in 0.5 mm×0.5 mm sections using a McIlvain tissue chopper (The Nickle Laboratory Engineering Co., Gomshall, Surrey, England). The resulting pieces of cerebellum are transferred to 100 ml of Krebs/bicarbonate buffer at 37° C. which is continuously equilibrated with 95:5 $O_2/CO_2$. The pieces of cerebellum are incubated in such a manner for ninety minutes with three changes of the buffer. The buffer then is decanted, the tissue centrifuged (1 min., 3200 r.p.m.) and the tissue resuspended in 20 ml of the Krebs/bicarbonate buffer. Then, 250 μl aliquots (approximately 2 mg) are removed and placed in 1.5 ml microfuge tubes. To those tubes are added 10 μl of the compound under study from a stock solution followed, after a 10 minute incubation period, by 10 μl of a 2.5 mM solution of NMDA to start the reaction. The final NMDA concentration is 100 μM. Controls do not have NMDA added. The tubes are incubated for one minute at 3? ° C. in a shaking water bath and then 750 μl of a 50 mM Tris-Cl, 5 mM EDTA solution is added to stop the reaction. The tubes are Placed immediately in a boiling water bath for five minutes. The contents of each tube then are sonicated for 15 seconds using a probe sonicator set at power level three. Ten microliters are removed and the protein determined by the method of Lowry, Anal. Biochem. 100:201–220 (1979). The tubes are then centrifuged (5 min., 10,000 xg), 100 μl of the supernatant is removed and the level of cyclic GMP (cGMP) is assayed using a New England Nuclear (Boston, Massachusetts) cGMP RIA assay according to the method of the supplier. The data is reported as pmole cGMP generated Per mg. protein. Undesired hypotensive activity is also determined by known methods, for example, according to the methods of Carron et al., also cited above.

Such selective neuroprotective antiischemic and excitatory amino acid blocking activities reflect the valuable utility of the present compounds in the treatment of stroke, traumatic brain injury and degenerative CNS (central nervous system) disorders such as Alzheimer's disease, senile dementia of the Alzheimer's type, Parkinson's disease and Huntington's disease; without significant potential for a concurrent, undue drop in blood pressure. In the systemic treatment of such diseases with a neuroprotective amount of compounds of the formula (I), (II) or (III), the dosage is typically from about 0.02 to 10 mg/kg/day (1–500 mg/day in a typical human weighing 50 kg) in single or divided doses, regardless of the route of administration. Of course, depending upon the exact compound and the exact nature of the individual illness, doses outside this range may be prescribed by the attending physician. The oral route of administration is generally preferred. However, if the patient is unable to swallow, or oral absorption is otherwise impaired, the preferred route of administration will be parenteral (i.m., i.v.) or topical.

The compounds of the present invention are generally administered in the form of pharmaceutical compositions comprising at least one of the compounds of the formula (I), (II) or (III), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

The present invention is illustrated by the following examples, but is not limited to the details thereof.

EXAMPLE 1

5-[2-(4-Benzyl-4-hydroxypiperidino)propionyl]-2(1H,3H)-indolone 5-(2-Chloropropionyl)-2(1H,3H)-indolone (2.5 g, 11.2 mmol), 4-hydroxy-4-benzylpiperidine (2.1 g, 11.2 mmol), and triethylamine (1.56 ml, 11.2 mmol) were combined in ethanol and refluxed overnight. The mixture was cooled to room temperature and concentrated at reduced pressure. The residue was partitioned between ethyl acetate and water and the phases were separated. The aqueous layer was extracted with ethyl acetate and the combined organic phase was washed with brine, dried over calcium sulfate, and concentrated. The crude product was flash chromatographed on silica gel eluting first unreacted 5-(2-chloropropionyl) -2(1H,3H)-indolone with 1:1 ethyl acetate:hexane. Continued elution with ethyl acetate gave 3.6 g of product as a light brown foam. Recrystallization from ethyl acetate/hexane gave 1.23 g of purified title product. Less pure fractions from the column and mother liquors from the recrystallization were rechromatographed as above with 1:1 and then 3:1 ethyl acetate:hexane. Product fractions were triturated with ether/hexane to give 0.2 g more product for a total yield of 1.43 g, 34%; m.p. 188°-192° C.; NMR 8.22 (s, 1H), 8.08 (d, J=8 Hz, 2H), 7.99 (s, 1H), 7.31-7.13 (m, 5H), 6.89 (d, J=8 Hz, 1H), 4.03 (q, J=6.8 Hz, 1H), 3.57 (s, 2H), 2.72 (s, 2H), 2.72-2.58 (m, 3H), 2.46 (distorted t, 1H), 75-1.40 m, 4H), 1.26 (d, J=6.8 Hz, 3H), 1.23-1.19 (m, 1H).

Anal. calcd for $C_{23}H_{26}N_2O_3$: C, 72.99; H, 6.92; N, 7.40%.

Found: C, 72.68; H, 6.77; N, 7.28%.

EXAMPLE 2

5-[2S*-(4-Benzyl-4-hydroxypiperidino)-1S*-hydroxypropyl]-2(1H,3H)-indolone

The product from Example 1 (0.75 g, 1.98 mmol) was dissolved in 50 ml of hot ethanol and allowed to cool. The solution was added over 1-2 minutes to a slurry of sodium borohydride (0.113 g, 2.98 mmol) in ethanol (50 ml) with a 25 ml ethanol rinse. The mixture was stirred overnight. Water (2 ml) was added and the solvent was removed at reduced pressure. The residue was partitioned between ethyl acetate and water. Note that a small amount of dithionite was added to all aqueous washes to prevent air oxidation of the product. The organic layer was separated, washed with brine, dried over calcium sulfate and concentrated to a white solid. This material was recrystallized from ethanol to give 0.24 g of product. The mother liquors were flash chromatographed on silica gel with ethyl acetate elution to afford 0.19 g more product for a total yield of 0.43 g, 57%; m.p. 228°-229° C. NMR 7.66 (br s, 1H), 7.31-7.10 (m, 7H), 6.77 (d, J=8 Hz, 1H), 4.17 (d, J=10 Hz, 1H), 3.49 (s, 2H), 2.84 (dt, J=2.5, 11 Hz, 1H), 2.76 (s, 2H), 2.65-2.40 (m, 4H), 1.86-1.50 (m, 5H), 1.15 (s, 1H), 0.76 (d, J=6.5 Hz, 3H).

Anal. calcd for $C_{23}H_{28}N_2O_3$: C, 72.61; H, 7.42; N, 7.36%.

Found: C, 73.04; H, 7.50; N, 7.35%.

EXAMPLE 3

5-[2S*-(4-Hydroxy-4-phenylpiperidino)-1S*-hydroxypropyl]-2(1H,3H)-indolone

By the procedures of Examples 1 and 2, 4-hydroxy-4-phenylpiperidine was converted to present title product in 38% over-all yield. The product was purified by silica gel flash chromatography and trituration with ethyl acetate; m.p. 216°-218° C.; NMR 7.51 d, J=9 Hz, 3H—has NH proton in this signal), 7.36 (t, J=7.5 Hz, 2H), 7.24 (dt, J=1.2, 7.5 Hz, 2H), 7.17 (dd, J=1.2, 7.5 Hz, 1H), 6.78 (d, J=8 Hz, 1H), 4.22 (d, J=10 Hz, 1H), 3.51 (s, 2H), 3.08 (dt, J=2, 11 Hz, 1H), 2.7-2.48 (m, 5H), 2.24-1.98 (m, 2H), 1.83-1.70 br d, 2H), 1.49 (s, 1H), 0.82 (d, J=7 Hz, 3H).

Anal. calcd for $C_{22}H_{26}N_2O_3$: C, 72.11; H, 7.15; N, 7.64%.

Found: C, 72.23; H, 7.30; N, 7.30%.

EXAMPLE 4

5-[2S*-(4-Hydroxy-4-phenylpiperidino)-1S*-hydroxypropyl]-3-methyl-2(1H,3H)-indolone By the method of Examples 1 and 2, 5-(2-chloropropionyl)-3-methyl-2(1H,3H)-indolone and 4-hydroxy-4-phenylpiperidine were converted to present title product in 24% yield; m.p. 219°-220° C. (from ethyl acetate).

EXAMPLE 5

5-[2-(4-Hydroxy-4-phenylpiperidino)propionyl]-1-(p-toluenesulfonyl)indole 5-(2-Bromopropionyl)-1-(p-toluenesulfonyl)indole (1.67 g, 3.37 mmol, 83% purity) was dissolved in hot ethanol (100 ml) and 4-hydroxy-4-phenylpiperidine (0.6 g, 3.39 mmol) and triethylamine (0.94 ml, 6.74 mmol) were added. The mixture was refluxed overnight. The reaction was cooled and concentrated directly onto silica gel and flash chromatographed. Elution with 1:3 ethyl acetate:hexane removed 0.1 g of non-brominated ketone. Continued elution with 1:1 ethyl acetate hexane gave 1.47 g, 87% of the title product as a glassy orange solid. NMR 8.34 (s, 1H), 8.09 (d, J=9 Hz, 1H), 8.00 (d, J=8.5 Hz, 1H), 7.77 (d, J=8.5 Hz, 2H), 7.61 (d, J=3.5 Hz, 1H), 7.45 (d, J=9 Hz, 2H), 7.33-7.29 (m, 2H), 7.24-7.21 (m, 4H), 6.72 (d, J=3.5 Hz, 1H), 4.18 (q, J=7 Hz, 1H), 2.88-2.84 (m, 2H), 2.73-2.62 (m, 2H), 2.32 (s, 3H), 2.18-2.06 (m, 1H), 2.05-1.97 (m, 1H), 1.77-1.66 (m, 1H), 1.59-1.54 (m, 1H), 1.31 (d, J=7 Hz, 3H). IR 1679, 1605, 1375, 1289, 1260, 1169, 1126, 994. FAB HRMS calcd for $C_{29}H_{31}N_2O_4S$ (MH+): 503.2006. Observed m/e: 503.2023.

EXAMPLE 6

5-[2-(4-Hydroxy-4-phenylpiperidino)propionyl]indole

The product of the preceding Example (1.3 g, 2.75 mmol) was dissolved in methanol (50 ml) and potassium hydroxide (0.324 g, 5.79 mmol) was added all at once. The mixture was refluxed 6 hours, then cooled and the solvent removed at reduced pressure. The residue was partitioned between ethyl acetate and water. The phases were separated and the aqueous layer was extracted with ethyl acetate. The combined organic layer was washed with brine, dried over calcium sulfate and concentrated. The residue was flash chromatographed on silica gel with 1:1 ethyl acetate:hexane elution to give 0.719 g, 75% of present title product as a glassy solid; m.p. 60°-70° C. NMR 8.52 (s, 1H), 8.49 (br s, 1H), 8.00 (dd, J=1.5, 8.5 Hz, 1H), 7.49-7.41 (m, 3H), 7.35-7.21 (m, 4H), 6.67 (s, 1H), 4.30 (q, J=6.5 Hz, 1H), 2.89-2.85 (m, 3H), 2.66 (t, J=9.5 Hz, 1H), 2.23-2.07 (m, 2H), 1.77-1.65 (m, 2H), 1.38 (d, J=6.5 Hz, 3H). IR(CHCl$_3$) 3470, 2924, 1673, 1613, 1412, 1348, 1323, 1276, 1224, 1115. FAB HRMS calcd for $C_{22}H_{25}N_2O_4$ (MH+ ): 349.1918. Cbserved m/e: 349.1930.

EXAMPLE 7

5-[2S*-(4-Hydroxy-4-phenylpiperidino)-1S*-hydroxypropyl]indole

The product of the preceding Example was reduced according to the procedure of Example 2. Present title product was obtained as a fluffy white solid in 15% yield after silica gel chromatography and recrystallization from ethanol; m.p. 220.5°-221° C. NMR 8.16 (br s, 1H), 7.63 (s, 1H), 7.54 (d, J=8.5 Hz, 2H), 7.38 (t, J=7.5 Hz, 3H), 7.30-7.19 (m, 3H), 6.53 (s, 1H), 4.39 (d, J=10 Hz, 1H), 3.08 (dt, J=2, 11.5 Hz, 1H), 2.90-2.62 (m, 4H), 2.35-2.10 (m, 2H), 1.90-1.80 (m, 2H), 0.82 (d, J=6.5 Hz, 3H). IR(CHCl$_3$) 3475, 2922, 1731, 1376, 1250, 1201, 1038.

Anal. calcd for $C_{22}H_{26}N_2O_2$: C, 75.40; H, 7.48; N, 7.99%.

Found: C, 74.99; H, 7.47; N, 7.91%.

EXAMPLE 8

5-[2-(4-Benzyl-4-hydroxypiperidino)acetyl]-2(1H,3H)-indolone

A mixture of 5-(chloroacetyl)-2(1H,3H)-indolone (2.05 g, 9.78 mmol), 4-hydroxy-4-benzylpiperidine (1.87 g, 9.78 mmol), potassium carbonate (2.97 g, 21.49 mmol), and potassium iodide (0.08 g, 0.48 mmol) in acetonitrile (200 ml) was refluxed overnight. The reaction was cooled and filtered through a celite pad. The filtrate was concentrated to give an orange foam which was flash chromatographed on silica gel with ethyl acetate elution. This afforded 0.79 g of oily yellow solid product. NMR 9.41 (br s, 1H), 7.91 (d, J=8 Hz, 1H), 7.86 (s, 1H), 7.28-7.14 (m, 5H), 6.90 d, J=8 Hz, 1H), 3.76 (s, 2H), 3.52 (s, 2H), 2.78-2.73 (m, 4H), 2.43 {t, J=10.5 Hz, 2H}, 1.86-1.76 (m, 2H), 1.50 (br d, J=12 Hz, 2H), 1.36 (br s, 1H). IR(KBr) 2920, 2815, 1710, 1685, 1615, 1240, 1115. FAB HRMS calcd for $C_{22}H_{25}N_2O_3$ (MH+): 365.1867. Observed m/e: 365.1883.

EXAMPLE 9

5-[2-(4-Benzyl-4-hydroxypiperidino)-1-hydroxyethyl]-2(1H,3H)-indolone

Reduction was carried out on the product of the preceding Example according to the procedure of Example 2. The product was purified by flash chromatography and recrystallization from ethyl acetate to yield present title product as a tan solid in 18% yield; m.p. 168.5°-169.5° C. NMR 8.40 (br s, 1H), 7.35-7.17 (m, 7H), 6.80 (d, J=8 Hz, 1H), 4.66 (dd, J=3.5, 10 Hz, 1H), 3.50 (s, 2H), 2.89 (br d, J=11 Hz, 1H), 2.77 (s, 2H), 2.68-2.33 (m, 6H), 1.83-1.67 (m, 2H), 1.59-1.52 (m, 2H), 1.27 (br s, 1H). IR(KBr) 3420, 3170, 2945, 2820, 1705, 1625, 1490, 1320, 1115, 830, 707. FAB HRMS calcd for $C_{22}H_{27}N_2O_3$ (MH+): 367.2023. Observed m/e: 367.2061.

EXAMPLE 10

5-[2-(4-Hydroxy-4-phenylpiperidino)-1-hydroxyethyl]-2(1H,3H)-indolone

By the procedures of Examples 8 and 2, 4-hydroxy-4-phenylpiperidine was converted to present title product in 5% yield after flash chromatography and repeated recrystallization from methylene chloride/ether; m.p. 192°-194° C. IR(KBr) 3410, 3180, 2930, 2825, 1715, 1490, 705.

Anal. calcd for $C_{21}H_{24}N_2O_3 \cdot 0.5$ H$_2$O: C, 69.79; H, 6.97; N, 7.75%.

Found: C, 69.77; H, 6.52; N, 7.60%.

EXAMPLE 11

6-[2-(4-Hydroxy-4-phenylpiperidino)-1-hydroxyethyl]-2(3H)-benzoxazolone

By the procedures of Examples 8 and 2, 6-(2-chloroacetyl)-2(1H)-benzoxazolone and 4-hydroxy-4-phenylpiperidine were converted to present title product in 25% yield after recrystallization from ethanol/ether; m.p. 175°-177° C. NMR (methanol-d$_4$) 7.51 (dd, J=1.5, 8.5 Hz, 2H), 7.35-7.29 (m, 3H), 7.24-7.19 (m, 2H), 7.05 (d, J=8 Hz, 1H), 4.94-4.90 (m, 1H—becomes dd J=3, 8.5 Hz with D$_2$O wash), 2.96-2.90 (m, 2H), 2.80-2.57 (m, 4H), 2.19 (dq, J=4.5, 13 Hz, 2H), 1.74 (br d, J=14.5 Hz, 2H). IR(KBr) 3320, 3115, 2920, 2830, 1785, 1750.

EXAMPLE 12

6-[2S*-(4-Hydroxy-4-phenylpiperidino)-1S*-hydroxypropyl]-3,4-dihydro-2(1H)-quinolone By the procedures of Examples 1 and 2, 5-(2-chloropropionyl)-3,4-dihydro-2(1H)-quinolone and 4-hydroxy-4-phenylpiperidine were converted to present title product obtained as a white solid in 28% yield after flash chromatography and ethyl acetate recrystallization; m.p. 218°-219° C. NMR 7.92 (s, 1H), 7.52 (d, J=7.5 Hz, 2H), 7.38 (t, J=7.5 Hz, 2H), 7.28 (t partially obscured by NMR solvent peak, J=7 Hz, 1H), 7.20 (s, 1H), 7.14 (d, J=8 Hz, 1H), 6.70 (d, J=8 Hz, 1H), 5.27 (br s, 1H), 4.22 (d, J=10 Hz, 1H), 3.09 (t, J=11 Hz, 1H), 2.96 (t, J=7 Hz, 2H), 2.73-2.58 (m, 6H), 2.32-2.05 (m, 2H), 1.86 (br d, J=14 Hz, 2H), 1.57 (s, 1H), 0.84 (d, J=6.5 Hz, 3H).

Anal. calcd for $C_{23}H_{28}N_2O_3$: C, 72.60; H, 7.42; N, 7.36%.

Found: C, 72.16; H, 7.34; N, 7.29%.

EXAMPLE 13

5-[2S*-(3-(4-Chlorophenylthio)-8-azabicyclo[3.2.1]-oct-8-yl)-1S*-hydroxypropyl]-2(1H,3H)-indolone By the procedures of Examples 1 and 2, 3-(4-chlorophenylthio)-8-azabicyclo[3.2.1]octane was converted to present, ether triturated title product in 7% yield as a 1:1 mixture with the corresponding 1R*,2S*-isomer; m.p. 146°-158° C.

EXAMPLE 14

6-[2S*-(3-Phenylthio-8-azabicyclo[3.2.1]oct-8-yl) -1S -hydroxypropyl]-3,4-dihydro-2(1H)-quinolone By the procedures of Examples 1 and 2, 6-(2-chloropropionyl)-3,4-dihydro-2(1H)-quinolone and 3-phenylthio 8-azabicyclo[3.2.1]octane were converted to present title product in 15% yield, m.p. 144°-145° C. (from ethyl acetate).

EXAMPLE 15

5-Chloro-6-[2R*-(4-hydroxy-4-phenylpiperidino) -1S*-hydroxypropyl]-2(3H)-benzoxazolone By the procedures of Examples 1 and 2, 5-chloro -6-(2-chloropropionyl)-2(1H)-benzoxazolone and 4-hydroxy -4-phenylpiperidine were converted to present title product in 79% yield; m.p. 198°-199° C. (from ethanol).

EXAMPLE 16

5-[2S*-(3-Hydroxy-3-phenyl-8-azabicyclo[3.2.1]-oct-8-yl)-1S*-hydroxypropyl]-2(1H,3H)-indolone By the procedures of Examples 1 and 2, 3-hydroxy -3-phenyl-8-azabicyclo[3.2.1]octane is converted to present title product.

EXAMPLE 17

5-[2S*-(3-Benzyl-3-hydroxy-8-azabicyclo[3.2.1]-oct-8-yl)-1S*-hydroxypropyl]-2(1H,3H)-indolone By the procedures of Examples 1 and 2, 3-benzyl -3-hydroxy-8-azabicyclo[3.2.1]octane is converted to present title product.

EXAMPLE 18

Optical Resolution of 5-[2S*-(4-Hydroxy -4-phenylpiperidino)-1S*-hydroxypropyl]-2(1H,3H)-indolone

Method A

A mixture of (+) camphor sulfonic acid (232 mg, 1 mmol) and title product of Example 3 (366 mg, 1 mmol) was stirred in 25 ml of ethanol. A clear homogeneous solution was nearly obtained before the salt began to precipitate. After standing at ambient temperature overnight, the salt was collected, rinsed with ethanol and dried under a stream of nitrogen. The 460 mg of pink salt obtained in this manner was recrystallized from ethanol four times. The resulting product weighed 260 mg, and had m.p. 241°-242.5° C. and $[\alpha]_{Na} = +19.0°$ (c=0.295, methanol), indicating that it was only partially resolved.

Method B

To a mixture of $CH_2Cl_2$ (25 ml) and DMF (1 ml) were added title product of Example 3 (0.366 g, 1 mmol), dicyclohexyl carbodiimide (0.226 g, 1.1 mmol), 1-hydroxybenzotriazole (0.148 g, 1.1 mmol), 4-dimethylaminopyridine (0.134 g, 1.1 mmol), and N-tert-butyloxycarbonyl-L-alanine (0.189 g, 1 mmol). The mixture was stirred under a nitrogen atmosphere overnight. The homogeneous solution was diluted with ethyl acetate (25 ml) and filtered through Celite (TM) to remove dicyclohexyl urea. The filtrate was concentrated and taken up in ethyl acetate (150 ml). A second filtration removed still more urea-by-product. The filtrate was washed with aqueous bicarbonate, water 1N aqueous LiCl and brine. The organic phase was dried over calcium sulfate and concentrated to an oily foam. Flash chromatography on silica gel (50×100 mm (2×4 inches) packed with 50% ethyl acetate/hexane) gave upon elution with 75% ethyl acetate/hexane first 0.1 g of a nearly pure diastereomer of the alanine adduct. This was followed by 0.2 g of a mixture of the diastereomers and finally 0.1 g of a partially enriched sample of the other diastereomer. The 0.2 g sample was rechromatographed in the same fashion to afford another 0.06 g of the first pure diastereomer. The combined 0.16 g product was recrystallized from ethyl acetate/hexane to give 0.094 g of the adduct as a white solid; m.p. 189°-190° C. NMR (CDCl₃) 7 61 (br s, 1H—D₂O washes out), 7.48 (dd, J=1.5, 8 Hz, 2H), 7.37 (t, J=7.5 Hz, 2H), 7.34-7.18 (m, 3H), 6.83 (d, J=8 Hz, 1H), 5.76 (d, J=10 Hz, 1H), 5.19 (br d, J=7 Hz, 1H), 4.37 (br t, J=7 Hz, 1H), 3.54 (s, 2H), 3.06-2.90 (m, 2H), 2.84-2.52 (m, 3H), 2.16-1.88 (m, 2H), 1.82-1.69 (m, 2H), 1.52 (d, J=7 Hz, 3H), 1.40 (s, 9H), 0.78 (d, J=7 Hz, 3H). $[\alpha]_D = +69.5°$, c=0.295 in methanol.

Analysis calculated for $C_{30}H_{39}N_3O_6$: C, 67.02; H, 7.31; N, 7.82.

Found: C, 66.92; H, 7.46; N, 7.80.

This t-boc-alanine adduct (0.047 g, 0.087 mmol) was dissolved in 9 ml of a 0.32N solution of sodium methoxide (0.15 g of Na dissolved in 20 ml of methanol). The mixture was stirred 2 hours and the solvent was removed at ambient temperature under vacuum. The residue was taken up in ethyl acetate and extracted with aqueous bicarbonate and brine. The organic phase was dried over calcium sulfate and concentrated. The crude product was flash chromatographed on silica gel (1×2 inches). After flushing the column with 50% ethyl acetate/hexane, the fully resolved dextrorotatory product was eluted with ethyl acetate; 0.011 g (34%). $[\alpha]_D = +45.3°$, c=0.19 in methanol.

The opposite enantiomer was prepared in a similar manner from N-tert-butyloxycarbonyl-D-alanine but the coupling reaction employed carbonyl diimidazole. Carbonyl diimidazole (0.42 g, 2 mmol) was added all at once to a stirred solution of N-tert-butyloxycarbonyl-D-alanine (0.76 g, 2 mmol) in methylene chloride (80 ml). The mixture was stirred 1 hour; then Example 3 title product (0.366 g, 1 mmol) was added all at once and the reaction stirred overnight. The mixture was diluted with methylene chloride and extracted with aqueous bicarbonate. The organic phase was dried, concentrated and flash chromatographed on silica gel (2×7 inches). Elution with 25% ethyl acetate/hexane followed by 50% ethyl acetate/hexane gave 0.13 g of the desired diastereomer, recrystallized from ethyl acetate/hexane to yield 0.077 g of purified material; m.p. 187°-188° C. $[\alpha]_D = -64.1°$, c=0.17 in methanol. This was hydrolyzed with methanolic sodium methoxide as above to give present title product in 85% yield; $[\alpha]_D = -40.5°$, c=0.21 in methanol. Continued elution of the above flash chromatography gave the other diastereomer contaminated with the first product.

EXAMPLE 19

7-Fluoro-5-[2-(4-hydroxy-4-phenylpiperidino) propionyl]-2-(1H,3H)-indolone

A mixture of 7-fluoro-5-(2-chloropropionyl) -2(1H,3H)-indolone (1.0 g, 4.14 mmol), 4-hydroxy -4-phenylpiperidine (0.74 g, 4.17 mmol) and triethylamine (1.2 ml, 8.6 mmol) in anhydrous dimethylformamide was heated to between 70 and 90° C. for 3 hours. The mixture was poured into 1N aqueous LiCl and extracted with two portions of ethyl acetate. The combined organic phase was washed with 1N HCl, water and brine. The organic phase was dried over magnesium sulfate, filtered and concentrated to 1.6 g of a reddish solid. The crude product was purified by flash chromatography on silica gel (2×4 inches, 50% ethyl acetate/hexane eluent) to yield 0.58 g of the desired product. This product was further purified by recrystallization from acetonitrile/ether to give 0.2 g of light yellow solid; m.p. 197°-199.5° C. NMR (DMSO-d$_6$) 11.25 (s, 1H), 7.90 (d, J=11.6 Hz, 1H), 7.82 (s, 1H), 7.42 (d, J=7.2 Hz, 2H), 7.28 (t, J=7.4 Hz, 2H), 7.17 (t, J=7.2 Hz, 1H), 4.76 (s, 1H), 4.25 (q, J=6.6 Hz, 1H), 3.66 (s, 2H), 2.88-2.63 (m, 2H), 2.60-2.55 (m, 1H), 2.49-2.38 (m, 1H), 1.88 (dt, J=12.2, 4.3 Hz, 1H), 1.77-1.49 (m, 3H), 1.16 (d, J=6.6 Hz, 3H). The mother liquors were rechromatographed to afford another 0.15 g of product for a total yield of 0.35 g (22%).

Analysis calculated for $C_{22}H_{23}FN_2O_3$: C, 69.09; H, 6.06; N, 7.32.

Found: C, 68.36; H, 5.85; N, 7.31.

EXAMPLE 20

7-Fluoro-5-[2S*-(4-hydroxy-4-phenylpiperidino)-1S*-hydroxypropyl]-2(1H,3H)-indolone Sodium borohydride (0.033 g, 0.872 mmol) was dissolved in absolute ethanol (3 ml) and the ketone product from the above reaction (0.3 g, 0.78 mmol) was added all at once as a solid. The reaction was further diluted with 10 ml of ethanol. The mixture was stirred under nitrogen for 2 hours. The excess hydride was quenched with water and the mixture was concentrated. The residue was partitioned between ethyl acetate and water. The phases were separated and the organic layer was washed with brine, dried over magnesium sulfate and concentrated to a glassy solid. This material was flash chromatographed on silica gel (1×4 inches). Elution with 50% ethyl acetate/hexane and then 100% ethyl acetate gave 0.2 g of white solid. Further purification by recrystallization from acetonitrile/ethyl acetate gave 0.1 g (33%) of product as a white powder; m.p. 225°-227° C. NMR (DMSO-d$_6$) 10.83 (br s, 1H), 7.54 (d, J=7.3 Hz, 2H), 7.33 (t, J=7.6 Hz, 2H), 7.21 (t, J=7.3 Hz, 1H), 7.07 (t, J=5,3 Hz, 2H), 5.09 (br s, 1H), 4.82 (s, 1H), 4.26 (d, J=9.3 Hz, 1H), 3.56 (s, 2H), 2.97 (t, J=10.6 Hz, 1H), 2.62-2.56 (m, 4H), 2.12-1.92 (m, 2H), 1.63 (br d, J=12.9 Hz, 2H), 0.74 (d, J=6.6 Hz, 3H).

Analysis calculated for $C_{22}H_{25}FN_2O_3$: C, 68.73; H, 6.55; N, 7.29.

Found: C, 68.53; H, 6.31; N, 7.13.

EXAMPLES 21-29

By the methods of the preceding examples, the following additional compounds were prepared (showing yield in final step, melting point and solvent from which isolated).

21. 6-[1S*-Hydroxy-2S*(4-hydroxy-4-(4-methylphenyl) piperidino)propyl]-3,4-dihydro-2(1H)-quinolone; 4%; m.p. greater than 250° C. (ethanol).
22. 6-Chloro-5-[1S*-hydroxy-2S*(4-hydroxy-4-phenylpiperidino)propyl]-2(1H,3H)-indolone; 1.7%; m.p. 200°-203° C. (ether).
23. 5-[1S*-Hydroxy-2S*-(3-phenylthio-8-azabicyclo[3.2.1]-oct-8-yl)propyl]-2(1H,3H)-indolone; 12%; m.p. 159°-160° C. (ethyl acetate/acetonitrile).
24. 5-[1R*-Hydroxy-2S*-(3-phenylthio-8-azabicyclo[3.2.1]-oct-8-yl)propyl-2(1H,3H)-indolone; 7%; m.p. 211°-212° C. (ethyl acetate/acetonitrile).
25. 7-Fluoro-5-[1S*-hydroxy-2S*(4-hydroxy-4-phenylpiperidino)propyl]-2(1H,3H)-indolone; 33%; m.p. 225°-227° C. (ethyl acetate/acetonitrile).
26. 4-Chloro-5-[1S*-hydroxy-2S*(4-hydroxy-4-phenylpiperidino)propy.1]-2(1H,3H)-indolone; 31%; m.p. 231°-233° C. (ethanol/ether).
27. 4-Chloro-5-[1R*-hydroxy-2S*(4-hydroxy-4-phenylpiperidino)propyl]-2(1H,3H)-indolone; 14%; m.p. 213.5°-218° C. (ethanol/ether).
28. 5-[1S*-hydroxy-2S*-(4-hydroxy-4-phenylpiperidino) propyl]-7-methyl-2(1H,3H)-indolone; 14%; m.p. 227.5°-230° C. (ethanol/dimethylsulfoxide).
29. 5-[1S*-hydroxy-2S*-(4-hydroxy-4-phenylpiperidino) propyl]-4-methyl-2(1H,3H)-indolone; 22%; m.p. 241°-242° C. (ethanol/dimethylsulfoxide).

PREPARATION 1

5-Cyano-1-(p-toluenesulfonyl)indole

Sodium hydride (8.4 g, 210 mmol) was washed twice with hexane and then suspended in tetrahydrofuran (500 ml). 5-Cyanoindole (20 g, 140 mmol) in tetrahydrofuran (200 ml) was added dropwise. The resulting mixture was stirred at ambient temperature for 1 hour and then p-toluenesulfonyl chloride (26.7 g, 140 mmol) in tetrahydrofuran (200 ml) was added. The reaction was stirred 3 hours more followed by addition of water. The phases were separated and the aqueous phase was extracted twice with ethyl acetate. The combined organic phase was washed with brine, dried over calcium sulfate and concentrated. The residue was recrystallized from ether to afford 29.97 g, 72% of title product; m.p. 129°-131° C.; NMR 8.04 (d, J=8.5 Hz, 1H), 7.85 (d, J=1 Hz, 1H), 7.75 (d, J=9 Hz, 2H), 7.67 (d, J=3.5 Hz, 1H), 7.53 (m, 1H), 7.23 (m, 2H), 6.68 (d, J=3.5 Hz, 1H), 2.34 (s, 3H). IR(CHCl$_3$ solution) 2225, 1597, 1453, 1380, 1289, 1266, 1169, 1138, 1123, 1089 (shoulder), 990. FAB HRMS calcd for $C_{16}H_{13}N_2O_2S(MH^+)$: 297.0669. Observed m/e: 297.0685.

PREPARATION 2

5-Propionyl-1-(p-toluenesulfonyl)indole

The product of the preceding Preparation (11.4 g, 40 mmol) was dissolved in dry toluene (760 ml) and chilled to 0° C. Ethylmagnesium bromide (14 ml, 42 mmol, 3 M) in 40 ml of dry toluene was added dropwise. The mixture was warmed to 58° C. for 24 hours, cooled, and quenched with water (60 ml) and 1N HCl (60 ml) with 0.5 hour stirring. The phases were separated and the aqueous layer was extracted 3 times with ethyl acetate. The combined organic phase was washed with brine, dried over calcium sulfate and concentrated. The residue was recrystallized from ethyl acetate to afford 6.8 g, 64% of present title product as a yellow solid; m.p. 162°-164° C. NMR 8.16 (d, J=1.5 Hz, 1H), 8.01 (d, J=8.5 Hz, 1H), 7.94 (dd, J=1.5, 8.5 Hz, 1H), 7.75 (d, J=8.5 Hz, 2H), 7.62 (d, J=3.5 Hz, 1H), 7.23 (d, J=8.5 Hz, 2H), 6.72 (d, J=3.5 Hz, 1H), 3.02 (q, J=7 Hz, 2H), 2.33 (s, 3H), 1.21 (t, J=7 Hz, 3H).

PREPARATION 3

5-(2-Bromopropionyl)-1-(p-toluenesulfonyl)indole

The product of the preceding Preparation (2.0 g, 6.12 mmol) was dissolved in chloroform (60 ml) and added dropwise to a suspension of cupric bromide (2.1 g, 9.4 mmol) in ethyl acetate (60 ml). The resulting mixture was refluxed overnight. The reaction was cooled and filtered through a celite pad and concentrated. The residue was recrystallized from ethyl acetate/hexane to afford 1.70 g, 69% of present title product as a brown solid. NMR analysis of this material showed it to be a 83/17 mixture of product and starting material which was used in the coupling reaction without further purification. NMR signals of the product: 8.22 (d, J=1.5 Hz, 1H), 8.04–7.91 (m, 2H), 7.77–7.73 (m, 2H), 7.62 (d, J=4 Hz, 1H), 7.24–7.19 (m, 2H), 6.73 (d, J=4 Hz, 1H), 5.31 (q, J=6.5 Hz, 1H), 2.32 (s, 3H), 1.87 (d, J=6.5 Hz, 3H).

PREPARATION 4

O-Methanesulfonyltropine

Tropine (14.2 g, 100 mmol) was dissolved in $CH_2Cl_2$ (210 ml) and triethylamine (23 ml, 160 mmol) was added. Methanesulfonyl chloride (9.3 ml, 120 mmol) was added rapidly dropwise which caused the methylene chloride solution to reflux gently. The mixture was stirred one hour further; then extracted with cold 0.5 molar sodium hydroxide, water, and brine, dried by filtration through phase separating paper and concentrated to yield 13.8 g (65%) of title product as a yellow solid. NMR 4.88 (t, J=5 Hz, 1H), 3.10–3.05 (m, 2H), 2.94 (s, 3H), 2.22 (s, 3H), 2.20–2.10 (m, 2H), 2.02–1.88 (m, 6H).

PREPARATION 5

3-Phenylthio-8-methyl-8-azabicyclo[3.2.1]octane

NaH (60% in oil; 2.77 g, 69 mmol) was washed with hexane (3x) and then suspended in tetrahydrofuran (300 ml). Thiophenol (6.5 ml, 63 mmol) in tetrahydrofuran (25 ml) was added dropwise over 5 minutes. The milky white suspension which formed, with hydrogen evolution, was stirred 10 minutes and then O-methanesulfonyltropine (13.8 g, 63 mmol in 25 ml of tetrahydrofuran) was added all at once. The mixture was refluxed overnight, cooled and filtered through diatomaceous earth with ether wash. The filtrate was diluted with ethyl acetate and washed with cold 1M NaOH, water, and brine, dried ($CaSO_4$) and concentrated to yield 11.48 g (78%) of title product as a yellow solid. NMR 7.50–7.18 (m, 5H), 3.32–3.21 (m, 1H), 3.15–3.09 (m, 2H), 2.25 s, 3H), 2.02–1.94 (m, 2H), 1.79–1.72 (m, 4H), 1.60–1.51 (m, 2H); $^{13}$C-NMR 134.8, 132.3, 128.8, 126.9, 61.16, 39.21, 38.38, 37.72, 26.42.

By the same method, 4-chlorothiophenol was converted to 3-(4-chlorophenylthio)-8-methyl-8-azabicyclo[3.2.1]-octane.

PREPARATION 6

3-Phenylthio-8-(2,2,2-trichloroethoxycarbonyl)-8-azabicyclo[3.2.1]octane

Title product of the preceding Preparation (11.48 g, 49.3 mmol) and $K_2CO_3$ (0.75 g, 5.4 mmol) were mixed with benzene (200 ml) and 2,2,2-trichloroethyl chloroformate (7.5 ml, 54.4 mmol) was added rapidly. The reaction was refluxed 2 hours, cooled, filtered, and concentrated. The orange oily residue was dissolved in $CH_2Cl_2$, washed with saturated $NaHC_3$ and then brine, dried ($CaSO_4$) and concentrated. The residue was purified by flash chromatography on silica gel (hexane and then 5% ethyl acetate/hexane elution) to give first unreacted thiophenol from the previous reaction and then title product as a yellow oil (13 g, 67%); NMR 7.42–7.23 (m, 5H), 4.72 (AB q, J=12 Hz, 2H), 4 35–4.30 (m, 4H), 2.73 (heptet, J=6 Hz, 1H), 2.05–1.68 (m, 6H). The oil was solidified by trituration with hexane; m.p. 83°–84.5° C.; Anal. C 48.47, H 4.58, N 3.49; calcd. C 48.68, H 4.60, N 3.55.

By the same method, the 4-chloro analog of the preceding Preparation was converted to 3-(4-chlorophenylthio)-8-(2,2,2-trichloroethoxycarbonyl)-8-azabicyclo -[3.2.1]octane.

PREPARATION 7

3-Phenylthio-8-azabicyclo[3.2.1]octane

Title product of the preceding Preparation (13.0 g, 33 mmol) was dissolved in acetic acid (400 ml) and zinc dust (11 g, 168 mmol) was added. The mixture was heated to 100° C. overnight, then concentrated and the residue partitioned between $CH_2Cl_2$ and saturated $NaHCO_3$. The resulting emulsion was cleared by filtration through diatomaceous earth. The phases were separated and the organic layer was dried through phase separating filter paper and concentrated to yield 6.1 g (84%) of title product as a yellow oil which solidified on standing; NMR 7.38–7.36 (m, 2H), 7.29–7.20 (m, 3H), 3.52 (s, 2H), 3.36 (heptet, J=6 Hz, 1H), 1.94–1.54 (m, 8H). $^{13}$C-NMR 134.0, 132.43, 128.83, 127.06, 54.93, 40.81, 39.01, 28.98.

By the same method, the 4-chloro analog of the preceding Preparation was converted to 3-(4-chlorophenylthio)-8-azabicyclo[3.2.1]octane.

PREPARATION 8

8-(2,2,2-Trichloroethoxycarbonyl)-3-endo-hydroxy-3-exo-phenyl-8-azabicyclo[3.2.1]octane 8-(2,2,2-Trichloroethoxycarbonyl)-8-azabicyclo -[3.2.1]octan-3-one (5.0 g, 16.6 mmol) was dissolved in ether (450 ml) and phenylmagnesium bromide (7.2 ml, 21.6 mmol, 3M in ether) was added dropwise over 5 minutes with stirring. A white precipitate formed and the mixture was stirred 30 minutes. Saturated ammonium chloride was added and the mixture was concentrated. The residue was taken up in methylene chloride and extracted with brine. The organic phase was further dried through phase separating filter paper and concentrated to yield title product as a thick yellow oil (5.94 g, 94%). This material was used in the next reaction without further purification.

The homologous 3-exo-benzyl derivative is prepared in like manner, substituting benzylmagnesium bromide for phenylmagnesium bromide.

PREPARATION 9

3-endo-Hydroxy-3-exo-phenyl-8-azabicyclo[3.2.1]octane

The entire title product from the preceding Preparation was dissolved in tetrahydrofuran (100 ml) and added to a mixture of zinc dust (45 g, 688 mmol) and 1M aqueous monopotassium phosphate (45 ml). The mixture was stirred for 3 days. Water (100 ml) was then added and the pH was adjusted to about 10 by the addition of solid sodium carbonate. The mixture was filtered through Oelite (TM) and concentrated to give 1.85 g (58%) of present title product as a white solid. Integration of the NMR spectrum for the bridgehead protons of this product showed it to be a 92:8 mixture of the desired product (δ 3.6) and its 3-endo phenyl isomer (δ 3.85). This mixture was used as is for the coupling reactions as separation of the coupled products is facile. $^{13}$C-NMR (300 MHz, CDCl$_3$)delta: 150.42, 128.15, 126.57, 124.52, 73.33, 54.45, 46.62, 29.29. The minor isomer showed aliphatic $^{13}$C signals at δ 54.92, 50.99, 30.33, 30.16.

The homologous 3-exo-benzyl derivative is prepared in like manner.

I claim:

1. A racemic or optically active compound of the formula

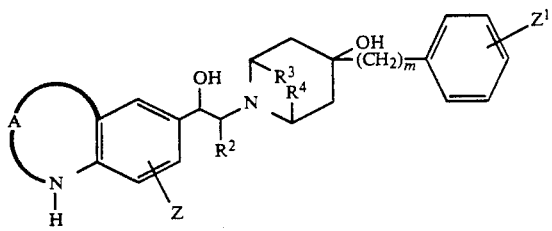

wherein

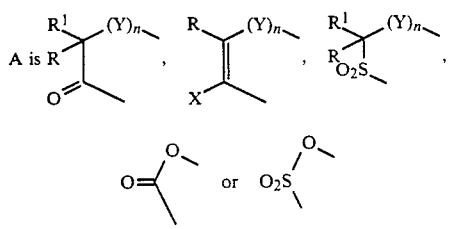

n is 0 or 1;
m is 0 or an integer from 1-6;
R, R$^1$ and R$^2$ are each independently hydrogen or (C$_1$-C$_3$)alkyl;
R$^3$ and R$^4$ are taken separately and are each hydrogen, or R$^3$ and R$^4$ are taken together and are ethylene;
X is hydrogen, (C$_1$-C$_3$)alkoxy or [(C$_1$-C$_3$) alkoxy]-carbonyl;
Y is CH$_2$ or oxygen;
Z and Z$^1$ are each independently hydrogen, (C$_1$-C$_3$)alkyl, (C$_1$-C$_3$)alkoxy, fluoro, chloro or bromo;
or a pharmaceutically-acceptable acid addition salt thereof.

2. A compound of claim 1 wherein R$^3$ and R$^4$ are taken separately and are each hydrogen.

3. A compound of claim 1 wherein m is 0 or 1, Z and Z$^1$ are each hydrogen and R$^2$ is hydrogen or methyl.

4. A compound of claim 3 wherein R$^3$ and R$^4$ are taken separately.

5. A compound of claim 4 wherein R$^2$ is methyl having the relative stereochemical formula

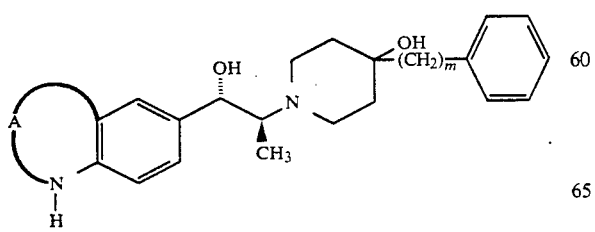

6. A compound of claim 5 wherein A is

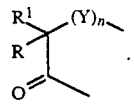

7. A compound of claim 6 wherein n is 0.
8. A compound of claim 7 wherein m is 1 and R and R$^1$ are each hydrogen.
9. A compound of claim 7 wherein m is 0.
10. The racemic compound of claim 9 wherein R and R$^1$ are each hydrogen.
11. An optically active compound of claim 9 wherein R and R$^1$ are each hydrogen.
12. A compound of claim 6 wherein n is 1 and Y is CH$_2$.
13. A compound of claim 12 wherein R and R$^1$ are each hydrogen and m is 0.
14. A compound of claim 5 wherein A is

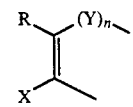

15. A compound of claim 14 wherein n is 0.
16. A compound of claim 15 wherein R and X are each hydrogen and m is 0.
17. A compound of claim 5 wherein A is

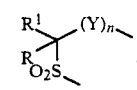

18. A compound of claim 17 wherein R and R$^1$ are each hydrogen and n and m are each 0.
19. A compound of claim 5 wherein A is

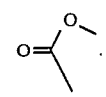

20. A compound of claim 19 wherein m is 0.
21. A compound of claim 5 wherein A is

22. A compound of claim 21 wherein m is 0.
23. A compound of claim 4 wherein R$^2$ is hydrogen.
24. A compound of claim 23 wherein A is

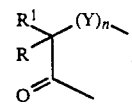

25. A compound of claim 24 wherein n is 0.
26. A compound of claim 25 wherein m is 0, and R and R$^1$ are each hydrogen.
27. A compound of claim 25 wherein m is 1, and R and R$^1$ are each hydrogen.
28. A compound of claim 23 wherein A is

29. A compound of claim 28 wherein m is 0.

30. A compound of claim 3 wherein $R^3$ and $R^4$ are taken together.

31. A compound of claim 30 wherein $R^2$ is methyl having the relative stereochemical formula

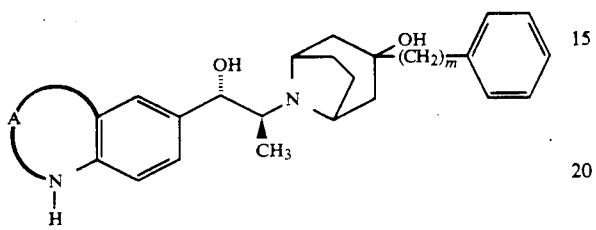

32. A compound of claim 31 wherein A is

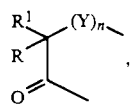

n is 0 and R and $R^1$ are each hydrogen.

33. A pharmaceutical composition comprising a neuroprotective amount of a compound of claim 1 and a pharmaceutically-acceptable carrier.

34. A pharmaceutical composition comprising a neuroprotective amount of a compound of claim 4 and a pharmaceutically-acceptable carrier.

35. A pharmaceutical composition comprising a neuroprotective amount of a compound of claim 30 and a pharmaceutically-acceptable carrier.

36. A method of treating stroke, traumatic brain injury or a CNS degenerative disease in man which comprises treatment with a neuroprotective amount of a compound of claim 1.

37. A method of treating stroke, traumatic brain injury or a CNS degenerative disease in man which comprises treatment with a neuroprotective amount of a compound of claim 4.

38. A method of treating stroke, traumatic brain injury or a CNS degenerative disease in man which comprises treatment with a neuroprotective amount of a compound of claim 30.

39. A compound of the formula

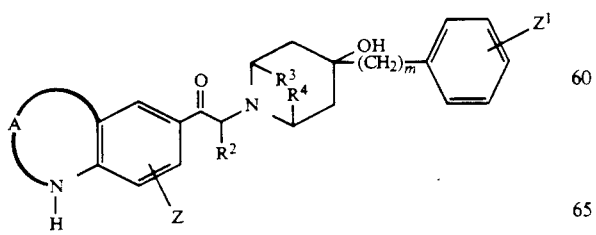

wherein

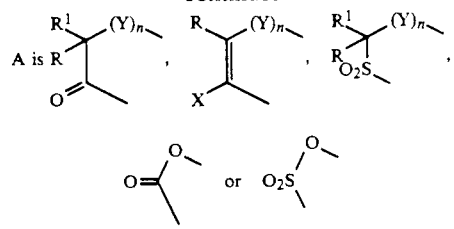

n is 0 or 1;
m is 0 or an integer from 1-6;
R, $R^1$ and $R^2$ are each independently hydrogen or $(C_1-C_3)$alkyl;
$R^3$ and $R^4$ are taken separately and are each hydrogen, or $R^3$ and $R^4$ are taken together and are ethylene;
X is hydrogen, $(C_1-C_3)$alkoxy or $[(C_1-C_3)$alkoxy]carbonyl;
Y is $CH_2$ or oxygen;
Z and $Z^1$ are each independently hydrogen, $(C_1-C_3)$alkyl, $(C_1-C_3)$alkoxy, fluoro, chloro or bromo.

40. A racemic or optically active compound of the formula

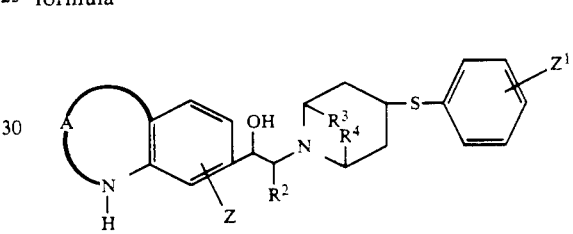

wherein

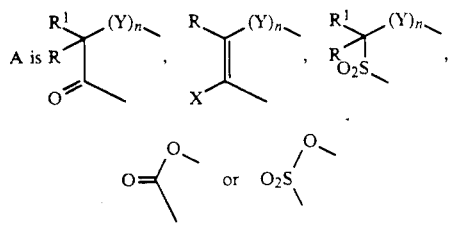

n is 0 or 1;
R, $R^1$ and $R^2$ are each independently hydrogen or $(C_1-C_3)$alkyl;
$R^3$ and $R^4$ are taken separately and are each hydrogen, or $R^3$ and $R^4$ are taken together and are ethylene;
X is hydrogen, $(C_1-C_3)$alkoxy or $[(C_1-C_3)$alkoxy]carbonyl;
Y is $CH_2$ or oxygen;
Z and $Z^1$ are each independently hydrogen, $(C_1-C_3)$alkyl, $(C_1-C_3)$alkoxy, fluoro, chloro or bromo; or a pharmaceutically-acceptable acid addition salt thereof.

41. A compound of claim 40 wherein A is

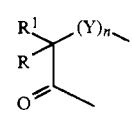

42. A compound of claim 41 wherein $R^3$ and $R^4$ are taken together.

43. A compound of claim 42 wherein $R^2$ is methyl having the relative stereochemical formula

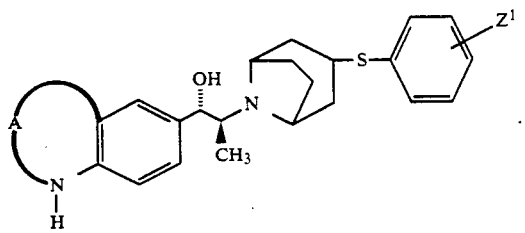

44. A compound of claim 43 wherein R and $R^1$ are each hydrogen and n is 0.

45. A compound of claim 44 wherein Z and $Z^1$ are each hydrogen or chloro.

46. A pharmaceutical composition comprising a neuroprotective amount of a compound of claim 40 and a pharmaceutically-acceptable carrier.

47. A method of treating stroke, traumatic brain injury or a CNS degenerative disease in man which comprises treatment with a neuroprotective amount of a compound of claim 40.

48. A compound of the formula

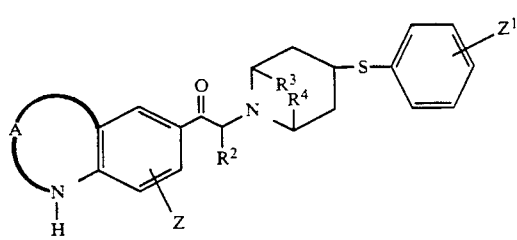

wherein

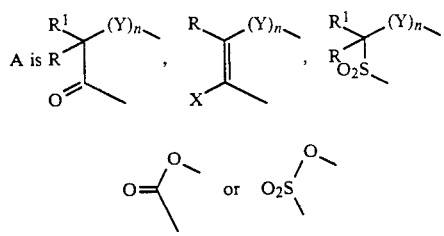

n is 0 or 1;

R, $R^1$ and $R^2$ are each independently hydrogen or $(C_1-C_3)$alkyl;

$R^3$ and $R^4$ are taken separately and are each hydrogen, or $R^3$ and $R^4$ are taken together and are ethylene;

X is hydrogen, $(C_1-C_3)$alkoxy or $[(C_1-C_3)$alkoxy]carbonyl;

Y is $CH_2$ or oxygen;

Z and $Z^1$ are each independently hydrogen, $(C_1-C_3)$alkyl, $(C_1-C_3)$alkoxy, fluoro, chloro or bromo.

49. A racemic or optically active compound of the formula

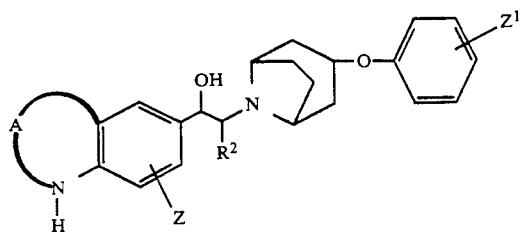

wherein

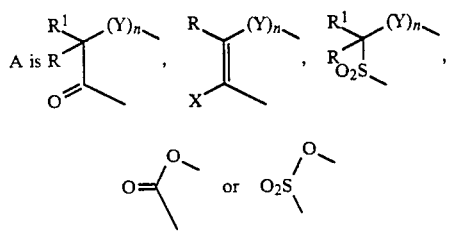

n is 0 or 1;

R, $R^1$ and $R^2$ are each independently hydrogen or $(C_1-C_3)$alkyl;

X is hydrogen, $(C_1-C_3)$alkoxy or $[(C_1-C_3)$alkoxy]carbonyl;

Y is $CH_2$ or oxygen;

Z and $Z^1$ are each independently hydrogen, $(C_1-C_3)$alkyl, $(C_1-C_3)$alkoxy, fluoro, chloro or bromo; or a pharmaceutically-acceptable acid addition salt thereof.

50. A compound of claim 49 wherein A is

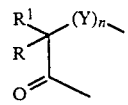

51. A compound of claim 50 wherein R and $R^1$ are each hydrogen.

52. A compound of claim 51 wherein Z is hydrogen and $Z^1$ is hydrogen or chloro.

53. A pharmaceutical composition comprising a neuroprotective amount of a compound of claim 49 and a pharmaceutically-acceptable carrier.

54. A method of treating stroke, traumatic brain injury or a CNS degenerative disease in man which comprises treatment with a neuroprotective amount of a compound of claim 49.

55. A compound of the formula

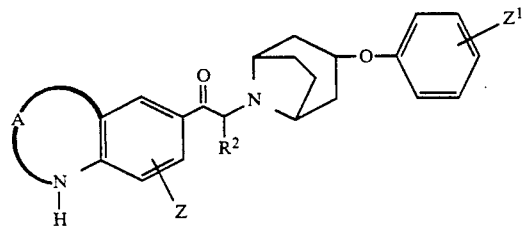

wherein

A is 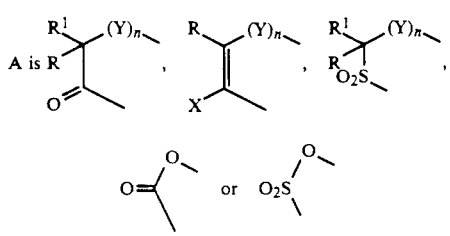
n is 0 or 1;
R, $R^1$ and $R^2$ are each independently hydrogen or $(C_1-C_3)$alkyl;
X is hydrogen, $(C_1-C_3)$alkoxy or $[(C_1-C_3)$alkoxy]carbonyl;
Y is $CH_2$ or oxygen;
Z and $Z^1$ are each independently hydrogen, $(C_1-C_3)$alkyl, $(C_1-C_3)$alkoxy, fluoro, chloro or bromo; or a pharmaceutically-acceptable acid addition salt thereof.
* * * * *